(12) United States Patent
Parakka et al.

(10) Patent No.: US 9,387,281 B2
(45) Date of Patent: Jul. 12, 2016

(54) PENDANT HYDROPHILE BEARING BIODEGRADABLE COMPOSITIONS AND RELATED DEVICES

(75) Inventors: James Parakka, AA Echt (NL); Ananth Iyer, AA Echt (NL)

(73) Assignee: DSM IP ASSETS B.V., TE Heerlen (NL)

( * ) Notice: Subject to any disclaimer, the term of this patent is extended or adjusted under 35 U.S.C. 154(b) by 133 days.

(21) Appl. No.: 13/880,666

(22) PCT Filed: Oct. 20, 2011

(86) PCT No.: PCT/EP2011/068379
§ 371 (c)(1),
(2), (4) Date: Oct. 23, 2013

(87) PCT Pub. No.: WO2012/052527
PCT Pub. Date: Apr. 26, 2012

(65) Prior Publication Data
US 2014/0037711 A1    Feb. 6, 2014

Related U.S. Application Data

(60) Provisional application No. 61/394,771, filed on Oct. 20, 2010.

(51) Int. Cl.

| | |
|---|---|
| *A61K 47/32* | (2006.01) |
| *A61K 47/34* | (2006.01) |
| *A61L 31/06* | (2006.01) |
| *A61L 31/16* | (2006.01) |
| *C08G 18/42* | (2006.01) |
| *C08G 63/00* | (2006.01) |
| *C08G 63/66* | (2006.01) |
| *C08G 63/664* | (2006.01) |
| *A61L 26/00* | (2006.01) |
| *A61L 31/04* | (2006.01) |
| *A61L 31/14* | (2006.01) |
| *A61L 15/58* | (2006.01) |
| *A61L 15/64* | (2006.01) |

(52) U.S. Cl.
CPC .................. *A61L 31/06* (2013.01); *A61L 15/58* (2013.01); *A61L 15/64* (2013.01); *A61L 26/009* (2013.01); *A61L 31/041* (2013.01); *A61L 31/048* (2013.01); *A61L 31/148* (2013.01); *A61L 31/16* (2013.01); *C08G 63/664* (2013.01)

(58) Field of Classification Search
CPC ..... A61L 31/06; A61L 31/041; A61L 31/048; A61L 15/58; A61L 15/64; A61L 26/009; A61L 31/148; A61L 31/16; C08L 71/02; C08L 39/06; C08G 63/664
See application file for complete search history.

(56) References Cited

U.S. PATENT DOCUMENTS

| | | | |
|---|---|---|---|
| 5,023,309 A * | 6/1991 | Kruse et al. | 528/49 |
| 6,696,499 B1 | 2/2004 | Cohn et al. | |
| 2005/0216074 A1 * | 9/2005 | Sahatjian et al. | 623/1.11 |
| 2009/0252777 A1 | 10/2009 | Taft et al. | |

FOREIGN PATENT DOCUMENTS

JP    2004-352911 A    12/2004

OTHER PUBLICATIONS

Lee et al., Macromolecules, 2008, 41, 4730-4738.*

* cited by examiner

*Primary Examiner* — Abigail Fisher
(74) *Attorney, Agent, or Firm* — Kevin M. Bull

(57) ABSTRACT

A composition comprising at least one polymer having the structure A-B-A', wherein A and A' may be the same or different and each is a degradable polyester component and wherein B is the reaction product resulting from the reaction between a diol, having one or more pendant oligomeric or polymeric groups, and A and A'. Additionally, a bioresorbable patch comprising: (a) an adhesion barrier component comprising the composition in the form of a film; and (b) an adhesive component comprising (i) at least one synthetic adhesive polymer and/or (ii) at least one polysaccharide. Also, a method of wound healing, comprising administering the composition or apply the patch to a patient.

13 Claims, 1 Drawing Sheet

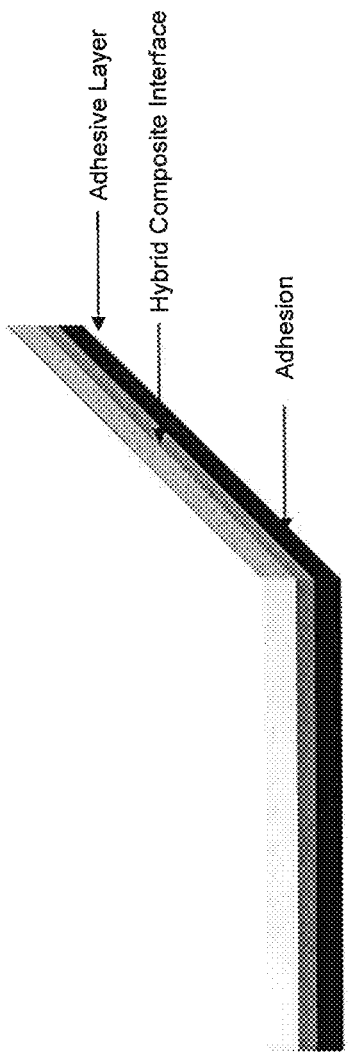
Figure 1. Composite bioresorbable adhesive patch construct

PENDANT HYDROPHILE BEARING BIODEGRADABLE COMPOSITIONS AND RELATED DEVICES

This application is the National Phase Under 35 U.S.C. §371 of PCT International Application No. PCT/EP2011/068379 which has an International filing date of Oct. 20, 2011, which claims priority to U.S. Provisional Application No. 61/394,771 filed on Oct. 20, 2010. The entire contents of all applications listed above are hereby incorporated by reference.

FIELD OF INVENTION

The instant invention relates to a composition comprising at least one polymer having the structure A-B-A', wherein A and A' may be the same or different and each is a degradable polyester component and wherein B is the reaction product resulting from the reaction between a diol, having one or more pendant oligomeric or polymeric groups, and A and A'.

Additionally, the invention also relates to the development of a bioresorbable patch comprising:
  (a) an adhesion barrier component comprising a composition according to the invention in the form of a film; and
  (b) an adhesive component comprising:
    (i) at least one synthetic adhesive polymer; and/or
    (ii) at least one polysaccharide.

The present invention provides a method of wound healing, comprising administering the composition or patch The instant invention further relates to bioresorbable polymers and particularly ones containing pendant and/or terminal oligomeric or polymeric end groups on a polymer backbone and biomedical devices made thereof. The backbone polymer can essentially be composed of bioresorbable polymers such as poly(hydroxy acids) and their derivatives that are linked, coupled, or chain extended to form functional polymers. Applications of these compositions include use as a barrier film for preventing post surgical adhesions, as a porous scaffold material for wound healing, and use as a medium to incorporate specific pharmaceutical compounds or biologically active components to support targeted therapeutic treatment.

BACKGROUND OF THE INVENTION

Poly(ethylene oxide) (PEO) and poly(propylene oxide) (PPO) are unique biocompatible polymers used in a variety of biomedical implant devices, such as controlled and targeted drug delivery systems, adhesion barriers, and tissue engineering applications. In an interesting commentary on a published paper by Sheth and Leckband (Sheth, S. R. and Leckband, D. Measurements of attractive forces between proteins and end-grafted poly(ethylene glycol) chains, Proc. Natl. Acad. Sci., 94, 8399-8404 (1997)) by Israelachvili (Israelachvili, J., The different faces of poly(ethylene glycol), Proc. Natl. Acad. Sc., 94, 8378-8379 (1997)), he discusses the characteristics of PEO, especially with regards to miscibility in aqueous media, ability to repel proteins and being repelled by proteins while enabling the dissolution and controlled release of drugs.

U.S. Pat. No. 6,677,362 discloses the use of solid dispersions of water-insoluble drugs in hydrophilic polymers, such as polyvinylpyrrolidone (PVP), or high molecular weight PEO, from aqueous solutions for improved bioavailability. U.S. Pat. No. 4,188,373 discloses the use of PEO-PPO-PEO block copolymers as sol-gel vehicles in pharmaceutical compositions that are soluble in water at room temperature, and has a gel transition temperature in the body temperature range (25-40° C.). The primary constraint of drug incorporation by this method arises from the severe differences in the water solubility of the polymer and the drug resulting in poor drug-loading capacity and efficiency.

U.S. Pat. No. 4,911,926 discusses the use of aqueous and non-aqueous compositions comprising polyoxyalkylene block copolymers in reducing post surgical adhesion formation. However. PEO and PPO are not biodegradable, and hence their use is restricted to low molecular weights so that they can be resorbed easily by the body. This seriously limits the use of PEO and PEO-PPO-PEO block copolymers by themselves as an adhesion barrier because low molecular weight PEO and PEO-PPO-PEO are absorbed at a much faster rate than the wound healing process. Also, low molecular weight PEO and PEO-PPO-PEO are soft materials and their applications are limited to biomedical areas where strength is not a requirement.

Aliphatic polyesters as medical implant devices have been studied extensively. Kulkarni, et al., discuss the development of synthetic bioresorbable polyesters produced by ring opening polymerization of L-lactide for implant studies (Kulkarni, et al., Biodegradable poly(lactic acid) polymers, J. Biomed. Mater. Res., Vol 5, 169-181, (1971)). These aliphatic polyesters are characterized by high strength (that can be processed into biomedical articles), low elongation, biocompatibility and degradation over a long period of time.

In an attempt to improve the biodegradability while not impacting on the tensile properties. U.S. Pat. No. 3,636,956 discloses the development of high strength aliphatic polyesters, viz. copolymers of L-lactide and glycolide that are fast degrading. Similarly, U.S. Pat. No. 4,438,253 discloses multiblock copolymers produced by transesterification of PEO and poly(glycolic acid) for use in surgical articles with good flexibility and faster biodegradability.

U.S. Pat. No. 4,826,945 discloses the synthesis of ABA type block copolymer composed of polyethylene oxide (PEO) and α-hydroxy carboxylic acid using a one-step process. The process essentially involves the ring opening polymerization of L-lactide, glycolide, caprolactone or other similar monomers using PEO of desired molecular weight and in the presence of catalyst at high temperatures. The ABA block copolymer generated is low molecular weight with terminal hydroxyl groups that is chain extended to very high molecular weights by reacting with a diisocyanate to yield polyetheresterurethane. Unlike polyesters that are rigid and having low extensibility, these polyetheresterurethanes are elastomeric, i.e. flexible and having high extension.

U.S. Pat. No. 4,826,945 discloses the use of $Sb_2O_3$ as the esterification catalyst for the ring opening polymerization, while the use of tin octoate as an efficient ring opening polymerization (esterification) catalyst has been reported in U.S. Pat. No. 3,839,297. U.S. Pat. No. 5,711,958 describes the sequential use of stannous octoate as a catalyst for the esterification reaction and chain extension reaction with a diisocyanate. The advantage of using stannous octoate as the esterification catalyst lies in its extended use as a catalyst in the subsequent polyurethane reaction.

U.S. Pat. Nos. 5,711,958; 6,136,333; 6,211,249, 6,696, 499; 7,202,281 further discuss the use of AB and ABA type polymers as adhesion barriers films in their hydrated form. However, significant amounts of PEO are required in the polymer to enable it to successfully function as an adhesion barrier. Even so, the efficacy of the entire polymeric material (in the form of films) to inhibit post surgical adhesions is limited and as much as one-third of the test population treated with these polymers reportedly developed severe adhesions The use of A-B, ABA and BAB type block copolymers, wherein, A=PEO or PEO-PPO and B=polyesters or poly (ortho esters) as bioresorbable drug delivery systems has been reportedly discussed in patent disclosures and journal literature. U.S. Pat. No. 4,526,938 discloses the use of ABA type of polyesters for use in tunable sustained release of drugs. By manipulating the amount of hydrophobic polyester component in the copolymer, it was possible to adjust the length of time for sustained drug release. U.S. Pat. No. 7,649,023 discloses the use of low molecular weight PEO in the development of oligomeric multiblock polyesters as free flowing liquid or water-reconstitutable drug carriers.

Whereas the above literature teaches the use of block copolymers containing poly(oxyalkylene) units for making different biomedical devices, there are other arrangements of the hydrophilic PEO units within the polymer structure that are recently being utilized for different applications. WO 2009/073192 A2 discloses the use of pendant side chain crystallizable (SCC) polymers as carriers for drug release applications. Polymeric release compositions with systems and methods for delivering release materials, for e.g. drugs and other bioactive materials have been described. In addition, use of the compositions as tissue scaffolds, ocular inserts, for delivery of nucleotides, and in drug eluting stent applications have been described.

A recent review article, (Neil Ayres (Ayres, N., Polymer brushes: Applications in biomaterials and nanotechnology, Polymer Chemistry, Vol 1, 2010, 769-777)) examines the uses of surface confined macromolecules or polymer brushes for surface and interface applications in areas of biomaterials and nanotechnology. As described earlier, pegylated surfaces (and other similar hydrophilic poly(oxyalkylene) amphiphiles) are "first approach" strategy for developing biocompatible devices. Leckband et al. (Leckband et al., Grafted (polyethylene oxide) brushes as non-fouling surface coatings, J. Biomater. Sci. Polymer Edn., 10(10), 1999, 1125-1147) describe the theoretical and quantitative aspects of grafted PEO brushes in preventing protein adsorption. They determined that controlling the graft density and molecular weight of PEO can be utilized to control, prevent or retard protein adsorption. Furthermore, the polymer segments of the grafted PEO brushes under hydrated conditions are predominantly amorphous.

Recently numerous accounts of using pendant side chain containing amphiphilic polyurethanes for improved control and stabilization of colloidal dispersions in aqueous media have been reported for non-medical applications. WO 2009013316 describes the use of pendant polyoxyalkylene based 1,3 diols (Tegomer D3403, Tegomer D 3123 and Tegomer D3409) in the preparation of a water-dispersible polyurethane using a polyisocyanate crosslinker. WO 2007023145 discloses the use of pendant MPEG based 1,3 diol for the synthesis of polyurethane dispersant coatings with good pigment dispersibility and stability.

The use of PVP as an adhesive for general purposes is known. Good adhesion to plastic surfaces, such as polyethylene terephthalate (PET) is disclosed in commercially available product literature, such as by BASF. U.S. Pat. No. 5,143,071 discloses the development of highly conducting non-stringy PVP and PEO based adhesive gels for application to skin to provide electrical contact for medical devices.

U.S. Pat. No. 7,727,547 describes a tissue adhesive formulation which consist of polymerizable and/or cross-linkable material in particulate form, the said material being in admixture with particulate material comprising tissue-reacting functional groups. The patent also describes application of such formulation to one side of a core of a naturally occurring or synthetic polymeric material. The adhesive polymer described in the patent comprises of reaction product of poly (N-vinyl-2-pyrrolidone-co-acrylic acid) copolymer and a reactant comprising a tissue-reacting functional group.

U.S. Pat. No. 5,508,036 claims a device for preventing adhesions which comprises a composite of a first layer and a second layer, each of which comprises a biodegradable polymer of different pore size and optionally with an adherence layer to support the adhesion barrier and to enable attachment of the device without suturing.

The object of the invention is the development of compositions comprising biodegradable amphiphilic polyesters have the advantage of retaining better mechanical integrity prior to onset of degradation in contrast to the ABA triblock biodegradable polymers according to the prior art described above.

This is achieved by a composition comprising at least one polymer having the structure A-B-A', wherein A and A' may be the same or different and each is a degradable polyester component and wherein B is the reaction product resulting from the reaction between a diol, having one or more pendant oligomeric or polymeric groups, and A and A'.

A further advantage of the compositions according to the invention is that the surface of a device manufactured from the compositions is hydrophilic or hydrophobic enriched and presents superior functional properties compared to the ABA triblock copolymers of the prior art. For example the polymers according to this invention can form a barrier for preventing post surgical adhesions.

Another advantage of the compositions according to the invention is that the amphiphilic property of the polymeric material in the compositions of the invention enables the dispersion and uniform distribution of bioactive agents in the polymer matrix. In this way the bioactive agents can released into the immediate tissue environment or intended site at a desired dose rate as the polymer degrades over the period of time.

Another advantage of the compositions according to the invention is that the ratio of the alkylene oxide units to the degradable ester linkages in the polymer composition allows tunability of the mechanical properties desired for a specific application.

Another advantage of the compositions of the present invention is that the compositions can be formed into a film which can be used in a bioresorbable adhesive patch containing a PVP based adhesive coated on the film of the composition according to the invention.

BRIEF DESCRIPTION OF THE DRAWINGS

FIG. 1 shows an example of an adhesive patch according to the present invention.

DETAILED DESCRIPTION

The instant invention relates to bioresorbable polymers, including ones containing pendant and/or terminal oligomeric or polymeric end groups on a polymer backbone and biomedical devices made therefrom. The backbone polymer is essentially composed of bioresorbable polymers such as poly(hydroxy acids) and their derivatives that are linked, coupled, or chain extended to form functional polymers. This invention also discloses application of the aforementioned biodegradable compositions in the biomedical field.

The invention relates more specific to a composition comprising at least one polymer having the structure A-B-A', wherein A and A' may be the same or different and each is a degradable polyester component and wherein B is the reaction product resulting from the reaction between a diol, having one or more pendant oligomeric or polymeric groups, and A and A'.

Preferably, A and A' each comprise a poly hydroxyl carboxylic acid. A or A' in the present invention preferably comprise poly(hydroxyl carboxylic acids), because these polymers will degrade and produce monomeric units which may be readily metabolized by the patient. The A or A' unit of the polymers may therefore also be referred to as "the degradable polyester", and generally may optionally include aliphatic polycarbonate segments. Aliphatic polycarbonate segments may include poly(alkylene carbonates) such as poly(trimethylene carbonate) that is known by one skilled in the art to be used as a component in the field of bioresorbable polymers.

The terms "poly(hydroxy carboxylic acid)" or "poly($\alpha$-hydroxy carboxylic acid)" are used to describe the polyester A and A' structures of A-B-A' structure used in polymeric compositions according to the present invention where A or A' is a polymeric polyester unit derived from an aliphatic hydroxy carboxylic acid or a related ester or dimeric ester. A and A' preferably are derived from an aliphatic $\alpha$-hydroxy carboxylic acid or related ester, including a cyclic dimeric ester. Examples of monomers that can be used to form the polyesters A and A' are lactic acid, lactide, glycolic acid, glycolide, or a related aliphatic hydroxycarboxylic acid or ester (lactone) such as, for example, $\epsilon$-caprolactone, $\delta$-glutarolactone, $\delta$-valerolactone, $\gamma$-butyrolactone, $\beta$-butyrolactone, $\beta$-propriolactone, 1,5-dioxepan-2-one, pivalactone, 1,4-dioxane-2-one, and mixtures, thereof. The $\alpha$-hydroxy acids and their corresponding cylic dimeric esters, especially lactide and glycolide can be used in the present invention Further the polymer comprises B, which is the reaction product resulting from the reaction between a diol, having one or more pendant oligomeric or polymeric groups, and A and A'. B may "result from" a diol or is the reaction product of a diol, containing a pendant oligomeric or polymeric group. As known to one of skill in the art, a pendant group or a side group is generally a cluster of molecules arranged in linear or branched conformations and attached to the backbone polymer chain.

For the purpose of this invention, the pendant moieties and their derivatives may be either hydrophobic or hydrophilic, and may generally include polyalkylene oxides, such as poly(ethylene glycol), poly(propylene glycol), PEO, PPO, PEO-PPO copolymers, mixtures thereof and their monoalkyl derivatives.

When B is hydrophobic, the desired pendant groups of the present invention include substantially linear alkyl and/or alkenyl hydrocarbons containing preferably alkyl and/or alkenyl groups comprising 3 to 30 carbon atoms (C3-C30 alkyl and/or alkenyl groups), more preferably between C5 to C25 and most preferably between C8 to C18. Examples of alkyl groups are, in particular, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl and so on. Suitable longer-chain C8-C30-alkyl or C8-C30-alkenyl groups are straight-chain and branched alkyl or alkenyl groups; for example octyl(ene), nonyl(ene), decyl(ene), undecyl(ene), dodecyl(ene), tridecyl(ene), tetradecyl(ene), pentadecyl(ene), hexadecyl(ene), heptadecyl(ene), octadecyl(ene), nonadecyl(ene).

For the purposes of the present invention, when B is hydrophilic, the pendant groups of choice are generally derived pendant oligomeric or polymeric oxyalkylene moiety, such as poly(ethylene glycol) (PEG), poly(propylene glycol (PPG), polyethylene oxide (PEO) and/or polypropylene oxided (PPO) and/or polyethylene oxide-polypropylene oxide (PEO-PPO) comprising groups, mixtures thereof and their monoalkyl derivatives.

The pendant group of B in the polymer A-B-A' preferably comprises a hydrophilic group.

More preferably, the pendant group in B comprises a polyvinylpyrrolidone (PVP) or poly(dimethylacrylamide) (PDMA) group, is a The terms "poly(ethlyene glycol)", "poly(oxyethylene)" and "polyethylene oxide" are used interchangeably in reference to the present invention.

The term "resulting from" or "derived from" is intended to mean "made from" through single or multiple chemical reaction steps and the term "derivative" is intended to mean different examples or analogues of a general chemical composition.

In the present invention, the A-B-A' structure is a unit which is generally derived from poly(hydroxy acid) polymers in the A block and poly(oxyalkylene) polymers in the B unit. The A block and the A' block of the A-B-A' structure of the present polymers are biodegradable and ranges in size from one monomeric unit up to about 200 or more monomeric units, with a preferred size ranging from about 4 to about 50 units, more preferably about 6 to about 30 units, even more preferably about 8 to 16 units. The A block preferably is derived from an alpha-hydroxy acid or a related ester or lactone which produces monomer units of alpha-hydroxy acid within the polymeric chain as will be described in greater detail below. More preferably the A block is derived from units of glycolic acid, lactic acid (preferably L, or D, L mixtures to promote bioabsorbability) or mixtures thereof, in the form of glycolide or lactide reactants (dimeric $\alpha$-hydroxy acids as explained in greater detail herein below). The B unit preferably comprises a diol precursor containing pendant poly(ethylene oxide) or poly(ethylene oxide-co-propylene oxide) copolymers. The B unit may vary in size from about 200 Da (dalton units) up to about 200,000 Da or higher, with a preferred range of about 1,000 Da up to about 20,000 Da. Most preferably, the B unit has a pendant poly(ethylene oxide) ranging in size from about 3,000 to about 10,000 Da. It is unexpectedly that the poly(ethyleneoxide) B unit provides the greatest inhibition or reduction in adhesion in the present invention.

The present bioresorbable polymers can be chain extended and/or end-capped. For instance, the present polymers are preferably end-capped with hydroxyl groups and are chain-extended using difunctional chain extenders such as diisocyanates, dicarboxylates, diesters or diacyl halide groups in order to chain extend the A-B-A' structure into high molecular weight polymer chains. Examples of aliphatic diisocyanates include 1,2-diisocyanatoethane, 1,4-diisocyanatobutane, 1,5-diisocyanatopentane, 1,6-hexamethylene diisocyanate, lysine ester diisocyanate, Tetramethylxylylenediisocyanate (TMXDI), isophorone diisocyanate, hydrogenated methylenediphenyldiisocyanate (HMDI) and other diisocyanates known to those skilled in the art or any combination of these. Examples of the an aromatic diisocyanates include toluene diisocyanate, methylenediphenyldiisocyanate (MDI), and other diisocyanates known to those skilled in the art or any combination of these. The chain-extenders may be multifunctional chain extenders containing isocyanate reactive groups, such as for e.g. hydroxyl, carboxylic acid, thiol, oxiranes, or amines. Other specific examples include trimethylol propane, pegylated amines, alcohols, thiols, amino acids, and oligomers such as trilysine.

Preferably, one or more polymers with the structure A-B-A', according to the invention are chain extended with a diisocyanate compound to form a polyesterurethane.

Alternatively, the polymers may be end-capped with groups such as carboxylic acid moieties or ester groups (which may be reacted directly as ester groups, activated as "active" ester groups or converted to active acyl groups such as acyl halides) or isocyanate groups and then reacted with difunctional chain extenders such as diols, diamines, or hydroxylamines among others, to produce chain extended polymers having high molecular weight. The isocyanates used in the end-caps are generally monofunctional, and include alkyl isocyanates such as octyl isocyanate and decyl isocyanate, or alkoxy isocyanates such as monofunctional PEG isocyanate. The polymers of the present invention may alternatively have a non-reactive end group, which is non-reactive with other chemicals in the polymer or composition.

Preferably, the polymers according to the present invention are end-capped with a monofunctional isocyanate compound.

The term "chain-extended" is used to describe polymers according to the present invention wherein the basic triblock is reacted with a difunctional chain-extender to increase the molecular weight of the present polymers. The present polymers are chain-extended to provide sufficiently high molecular weight polymer chains to enhance the strength and integrity of the final polymer compositions as well as affecting the rate of degradation. It is noted that chain extension of the polymers provides adequate strength and integrity of the final films and other structures, yet allows a degree of mobility of the individual polyoxyalkylene present in the B units within the A-B-A' structure in order to maximize the adhesion inhibiting characteristics of the films. The chain extenders which are used are difunctional compounds which react with the end-cap group of the A-B-A' structures to produce the chain extended A-B-A' structures according to the present invention. In the present invention, the amount of chain extender which is included within the polymers according to the present invention may vary. Thus, the molar ratio of chain extender to A-B-A' structure in the present polymers varies from about 0.5 to about 2.0 (about 1:2 to about 2:1, based upon the number of moles of difunctional chain extender and the number of moles of A-B-A' polymer), more preferably about 0.8 to about 1.2 and most preferably about 1.0. It is noted that in synthesizing the present chain-extended polymers, the mount of chain extender which is reacted with difunctional triblock to produce polymer, is generally slightly higher than the amount which is expected to be included in the final synthesized polymers. Chain extenders which are used in the present invention, preferably contain no more than about 1% by weight of a crosslinking compound (such term signifying a compound containing at least 3 functional groups which can react with the end-cap group of the triblock and which generally appear in a chain extender sample as a side product of the synthesis or production of the chain extender), more preferably, less than about 0.5% by weight of a trifunctional compound and even more preferably less than 0.1% by weight. It is most preferable to employ a difunctional chain extender which contains as little trifunctional (or higher functionality) compound as is practical. Also, the occurrence of side reactions which would lead to crosslinking of the polymers is negligible, due to both compositional as well as experimental parameters of the synthesis of the polymers of the present invention.

The present polymers may contain self assembling groups. Self assembling groups can be one or more chemical groups, polymers or oligomers, such as aliphatic alkyl oligomers. Self assembling end groups are discussed in published U.S. Application 2009/0258048 A1, the entire contents of which are hereby incorporated by reference. Self assembly of the present polymers may be enabled by intermolecular and/or intramolecular non-covalent binding forces.

Bioresorbable and biodegradable refer to the characteristic whereby a polymer will degrade hydrolytically, oxidatively or enzymatically in the body. The polymers according to the present invention readily hydrolyze in vivo and breakdown readily into monomeric units of hydroxy acids. In the case of the PEG chains in the B unit, although these are not biodegradable, they are readily excreted by the patient upon degradation of the A block. The degradation of the present polymers primarily occurs through the hydrolysis of the ester bond in the A block under body physiological pH conditions. The hydrolysis reaction is generally dependent upon pH. The rate constant for hydrolysis tends to be much higher at high pH (greater than 9.0) and low pH (less than 3.0) than at neutral pH (6.0 to 8.0). The rate constant for hydrolysis tends to be higher under basic conditions than under acidic conditions.

The degradation properties of the present polymers are "tunable". The rate of hydrolytic degradation can be slowed substantially by using the hydrophobic pendant groups or by using esters derived from ε-caprolactone, δ-glutarolactone, δ-valerolactone, γ-butyrolactone, β-butyrolactone, β-propriolactone, 1,5-dioxepan-2-one, pivalactone, 1,4-dioxane-2-one and mixtures thereof. Likewise, the rate of hydrolysis can be accelerated by using hydrophilic pendant groups, such as PEO, PPO, PEO-PPO copolymers, PVP. PDMA, phosphoryl choline or by using esters derived from L-lactide, D,L-lactide, glycolide and mixtures thereof.

The presence of hydrophilic poly(alkylene oxide) units as pendant groups with or without terminal hydrophilic moieties in the relatively hydrophobic polymeric back bone is capable of imparting amphiphilic properties that are suitable in biomedical device applications. In addition, the polymers of this invention have the advantage of retaining better mechanical integrity prior to onset of degradation in contrast to the ABA triblock biodegradable polymers known in the art. Furthermore enrichment of the surface of a device manufactured from polymers of this invention can present superior functional properties compared to the ABA triblock copolymers of the prior art. For example the polymers according to this invention can form a barrier for preventing post surgical adhesions. The amphiphilic property of the polymeric material enables the dispersion and uniform distribution of active agents in the polymer matrix. The bioactive agent(s) loaded polymer matrix can be converted into a biomedical device, such as an adhesion barrier or a tissue scaffold and optionally implanted at the wound site. The bioactive agents are released into the immediate tissue environment or intended site at a desired dose rate as the polymer degrades over the period of time.

The ratio of the alkylene oxide units to the degradable ester linkages in the polymer composition allows tunability of the mechanical properties desired for a specific application.

The term "EO/LA ratio" is used to describe the relative amount of poly(ethylene oxide) and/or poly(ethylene oxide)-co-poly(propylene oxide) with respect to hydroxy carboxylic acid (preferably, α-hydroxy carboxylic acid, most preferably, lactic acid) which is used in present polymers and chain-extended polymers according to the present invention. This term refers to the length (number of monomeric ethylene oxide units) of the B unit [preferably, poly(ethylene oxide)] divided by the total number of α-hydroxy acid units in both A blocks (preferably, lactic acid) of the polymer as described hereinabove. When the ratio measures the ratio of ethylene oxide: L-lactide, the ratio may be termed "EO/LLA". Polymers comprised of A-B-A' structure described above which are chain extended pursuant to the present invention are also described in terms of an EO/LLA ratio. Polymers according to the present invention can have EO/LA ratios ranging from about 0.05 to about 100, or preferably about 0.1 to about 20, or more preferably about 0.25 to about 6.

The inherent water absorbing capacity of poly(alkyleneoxides) such as poly(ethylene oxide) present in the compositions of this invention and selection of the biodegradable hydroxy acid groups in the polymers of this invention facilitate tunability of the degradation behavior for a specific targeted application. Frequently, the "water absorbing capacity" is affected by the hydrophilicity of a chain extender or an end group. Specifically "water absorbing end groups" may include PEO, PPO, PEO-PPO copolymers, PVP, PDMA, phosphoryl choline and other natural and synthetic polymers known to those skilled in the art. "Non-water absorbing end groups" may include alkyl, silicon (or silicones), and fluorinated oligomers.

Furthermore, the presence of poly(ethylene oxide) segments in the polymers of this invention is important to support adhesion barrier properties in the hydrated form. See for example, U.S. Pat. Nos. 5,711,958; 6,136,333; 6,211,249; 6,696,499; and 7,202,281 which are incorporated by reference in their entirety. The term "adhesion" is used to describe abnormal attachments between tissues or organs or between tissues and implants (prosthetic devices) which form after an inflammatory stimulus, most commonly surgery, and in most instances produce considerable pain and discomfort. When adhesions affect normal tissue function, they are considered a complication of surgery. These tissue linkages often occur between two surfaces of tissue during the initial phases of post-operative repair or part of the healing process. Adhesions are fibrous structures that connect tissues or organs which are not normally joined. Common post-operative adhesions to which the present invention is directed include, for example, intraperitoneal or intraabdominal adhesions and pelvic adhesions. Adhesions can occur after all types of surgery including, for example, musculoskeletal surgery, abdominal surgery, gynecological surgery, ophthalmic, orthopedic, central nervous system, cardiovascular and intrauterine repair. Adhesions may produce bowel obstruction or intestinal loops following abdominal surgery, infertility following gynecological surgery as a result of adhesions forming between pelvic structures, restricted limb motion (tendon adhesions) following musculoskeletal surgery, cardiovascular complications including impairing the normal movement of the heart following cardiac surgery, an increase in intracranial bleeding, infection and cerebrospinal fluid leakage and pain following many surgeries, especially including spinal surgery which produces low back pain, leg pain and sphincter disturbance, By "adhesion barrier properties" or "adhesion barrier functionality" it is meant the ability to prevent adhesions following surgical procedures, such as in the extra vascular space. The adhesion barrier properties can be modified by selection of the molecular weight and by adjusting spatial density of the poly(ethylene oxide) segments in the pendant and the terminal end group. For instance, if a polymer is chain extended, which adds MW and spreads out the spatial distance between poly(ethylene oxide) segments between the pendant and terminal end groups, the polymer has a superior barrier to adhesion. The present polymers of the A-B-A' form represents adhesion barrier polymers due to the presence of these adhesion barrier properties.

Additionally, the composition may include bulk or surface property modifying additives. The bulk property is modified by incorporating suitable plasticizers, such as water, glycerol, sorbitol, PEO, PPO, PEO/PPO polymers, phthalate-based esters and other plasticizing esters known to those skilled in the art. The surface properties of a composition can be altered by providing "surface active compounds." Surface active compounds and surface modifying additives are disclosed in published U.S. Application 2009/0258048 A1 the entire contents of which are hereby incorporated by reference.

The term "homogeneous" is used to describe preferred polymers according to the present invention. The term homogeneous is associated with the inclusion in the final polymer compositions of a population of A-B-A' structures which are generally of the same size and preferably have a polydispersity of between about 1.0 and 4.0, more preferably about 1.1 to about 2.0 and even more preferably about 1.1 to about 1.6. Homogeneous A-B-A structures are associated with reproducible mechanical and physical characteristics and favorably consistent biodegradability.

The term "structure" is used to describe polymers according to the present invention by their molecular structure but also to describe a structure which has form, size and dimensions which are established outside the body and will not significantly change upon being placed inside the body of the patient to be treated. The term structure embraces not only flat surfaced structures (i.e., films) in the traditional manner, but also cylinders, tubes and other three dimensional structures which are not substantially changed by the anatomy of the patient into which the structure has been placed. Such structures may include porous constructs wherein the pore structure in the polymer matrix has well-defined size; geometry; and distribution. Besides, the aforementioned characteristics, the pores may be interconnected and the pore cells (each individual pore) may have an open cell structure. These controls on the pore structures facilitate cell proliferation into the polymer matrix followed by soft-tissue growth and ultimately organ repair. Porous constructs are achieved using a variety of techniques described in literature.

The term "gels" is used to describe dispersions or suspensions of polymer which have been formed by dissolving, suspending or dispersing polymer in an aqueous solution for delivery to a site in or on the patient's body in order to prevent adhesions. Gels of the present invention typically contain polymer in a sterile aqueous solution (such solution comprising saline solution, sterile water or a water/ethanol mixture) at a viscosity ranging from about 100 to about 100,000, or about 500 centipoises units up to a bout 20,000 centipoises units or more. The gels can be delivered in a sterile, isotonic saline solution at a viscosity ranging from about 2000 centipoises units up to about 20,000 centipoises units depending upon the application. In certain aspects according to the present invention, liquid polymeric compositions comprising non-water soluble polymers may also be used.

Gels according to the present invention may be used in numerous applications to reduce or prevent adhesions, and can be employed to reduce or prevent adhesions following general surgical procedures and related surgeries which are minimally invasive. Gels may utilize a non-water soluble A-B-A' structure, which is then chain-extended with water-soluble or hydrophilic chain extenders in order to render the overall polymeric composition water dispersible or water soluble. Certain phases within the gel polymer compositions will be advantageously non-water soluble in order to promote the structural integrity and reduce the overall rate of biodegradability of the gel formulations in the body.

The term "viscous solution or suspension" is used to describe solutions or suspensions of polymers according to the present invention wherein the solution has a viscosity which is greater than about 1 centipoises unit and is less than about 20,000 centipoises units, alternatively about 10 centipoises units to about 5,000 centipoises units, and alternatively about 100 centipoises units and above within this range. Viscous solutions or suspensions of polymers according to the present invention at viscosities approaching the high end of the range of viscosities may be indistinguishable from gels at the low end of a viscosity range. The present invention also contemplates liquid polymeric compositions having appropriate viscosity and flow characteristics and their use to reduce and/or prevent adhesions.

The term "foam" is used to describe open or closed cell porous solid forms wherein the pores within the solids are either fully or partially interconnected.

The present A-B-A' polymer structure can be used to form a "reactive prepolymer". A reactive prepolymer is a polymer that has not been completely reacted before being introduced or administered in an application, for example, to a patient to be treated.

Preferably, one or more polymers according to the present invention are reacted with an excess of diisocyanate to form a reactive polyesterurethane prepolymer.

More preferably, the prepolymer is reacted with water or a multifunctional chain extender group selected from the group consisting of an amino, hydroxyl, or thiol compound to generate a polyesterurethaneurea, polyesterurethane, and polyesterurethanethiourethane polymer.

The reactive prepolymer may polymerized in situ (i.e., at the site of administration) with a second component or may be polymerized as a result of reaction between the prepolymer and the tissue surface. In contrast, prepolymerized polymers of the present invention are utilized to create both preformed structures, e.g., compositions having three-dimensional structure such as films, cylinders, spheres, rods, blocks, tubes, beads, foam or rings, etc. and related structures, and non-preformed compositions such as sprays, gels, liquid polymers, pastes, viscous solutions and dispersions, among others.

General examples of bioresorbable polyesters, polyesterurethanes, and polyesterurethane ureas are depicted in Formula 1a-e.

Formula 1(a)

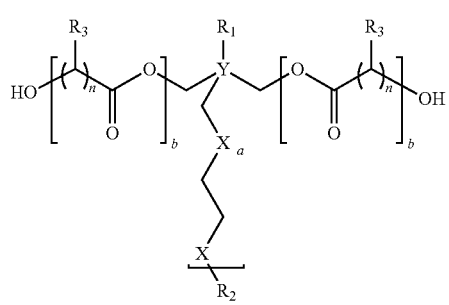

wherein X is O, S, or —CH$_2$—,

Y is C or N,

R$_1$ is H, an alkyl group containing 1-24 carbon atoms, a group containing an aromatic substituent, or a group containing multiple alkylene oxide units of up to 500 units, R$_2$ is alkyl group containing 1-12 carbon atoms.

R$_3$ is H, an alkyl group containing 1-24 carbon atoms, or an alkoxy group containing multiple alkylene oxide units of up to 500 units, n is 1-12, a is 2-500, and b is 1-100.

Formula 1(b)

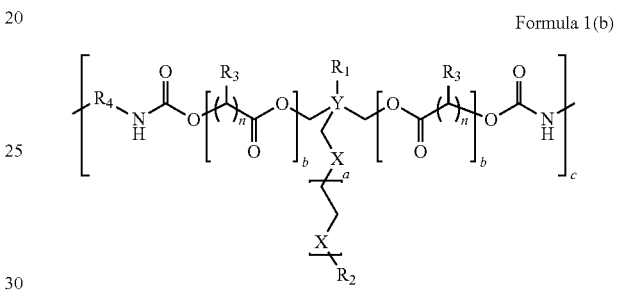

wherein X is O, S, or —CH$_2$—,

Y is C or N,

R$_1$ is H, an alkyl group containing 1-24 carbon atoms, a group containing an aromatic substituent or a group containing multiple alkylene oxide units of up to 500 units, R$_2$ is alkyl group containing 1-12 carbon atoms, R$_3$ is H, an alkyl group containing 1-24 carbon atoms, or an alkoxy group containing multiple alkylene oxide units of up to 500 units, R$_4$ is a diisocyanate reaction fragment, n is 1-12, a is 2-500, b is 1-100, and c is 1-200.

Formula 1(c)

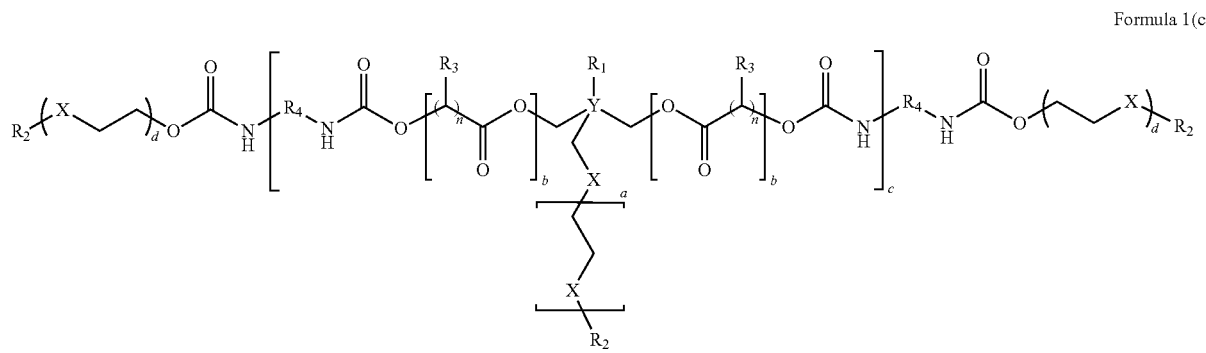

wherein X is O, S, or —CH$_2$—,
Y is C or N,
R$_1$ is H, an alkyl group containing 1-24 carbon atoms, a group containing an aromatic substituent, or a group containing multiple alkylene oxide units of up to 500 units,
R$_2$ is alkyl group containing 1-12 carbon atoms or a silicone containing fragment,
R$_3$ is H, an alkyl group containing 1-24 carbon atoms, or an alkoxy group containing multiple alkylene oxide units of up to 500 units,
R$_4$ is a diisocyanate reaction fragment,
n is 1-12,
a is 2-500,
b is 1-100,
c is 1-200, and
d is 4-300.

Formula 1(d)

wherein X is O, S, or —CH$_2$—,
Y is C or N,
Z is O, S, NH, or an N-alkyl group,
R$_1$ is H, an alkyl group containing 1-24 carbon atoms, a group containing an aromatic substituent, or a group containing multiple alkylene oxide units of up to 500 units,
R$_2$ is alkyl group containing 1-12 carbon atoms,
R$_3$ is H, an alkyl group containing 1-24 carbon atoms, or an alkoxy group containing multiple alkylene oxide units of up to 500 units,
R$_4$ is a diisocyanate reaction fragment,
R5 is an alkyl, silicone, alicyclic, heterocyclic, or an an aromatic group,
n is 1-12,
a is 2-500,
b is 1-100,
c is 1-20, and
d is 4-300.

wherein X is O, S, or —CH$_2$—,
Y is C or N,
R$_1$ is H or an alkyl group containing 1-24 carbon atoms, a group containing an aromatic substituent, or a group containing multiple alkylene oxide units of up to 500 units,
R$_2$ is alkyl group containing 1-12 carbon atoms or a silicone containing fragment,
R$_3$ is H. an alkyl group containing 1-24 carbon atoms, or an alkoxy group containing multiple alkylene oxide units of up to 500 units.
a is 2-500,
b is 1-100, and
d is 4-300.

When R$_1$ is an aromatic substituent it is preferably a phenyl group or a derivative thereof.

The alkylene oxide units are preferably poly(ethylene oxide) units.

Specific examples of bioresorbable polyesters, polyesterurethanes, and polyesterurethane ureas are depicted in Formula 2a-c.

Formula 2(a)

wherein a is 23 units, and
b is 40 units.

Formula 1(e)

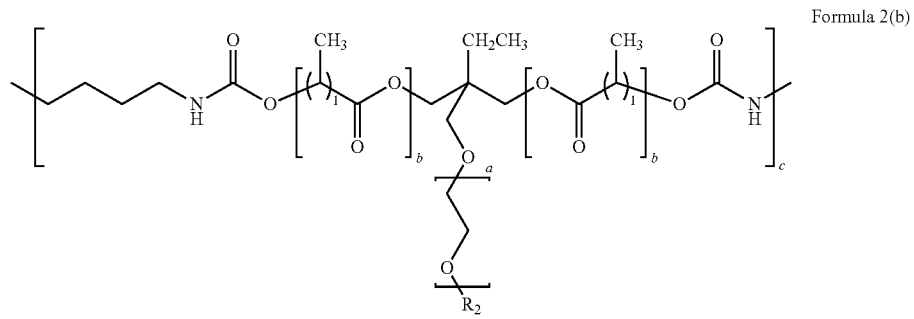

Formula 2(b)

wherein a is 23 units,
b is 40 units, and
c is 10 units.

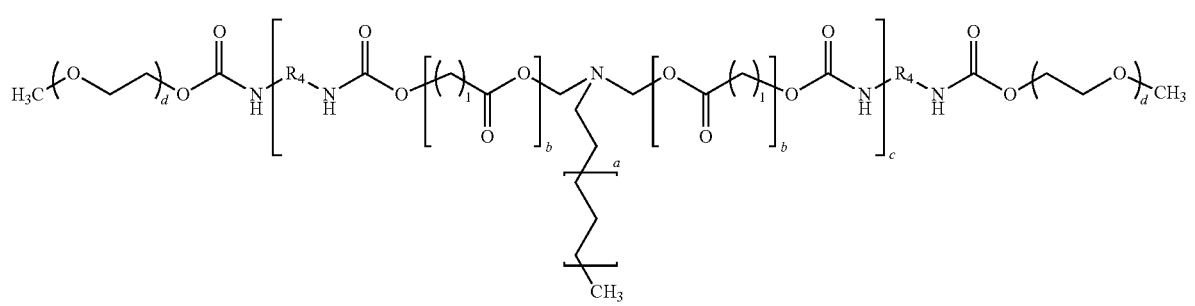

Formula 2(c)

wherein
$R_4$ is a diisocyanate reaction fragment,
a is 23 units,
b is 40 units,
c is 10 units, and
d is 114 units.

Use of the Polymers in Biomedical Applications

The present bioresorbable polymers can be formed into gels, films, and other structures including rods, cylinders, sponges, foams, dispersions, viscous solutions, liquid polymers, sprays or gels. Such structures can be implanted, administered topically, or administered by other means such as injection. Applications of the present polymers include implantable medical devices, physically crosslinked gels and chemically crosslinked adhesives using specifically designed prepolymers of the present structure. Structures using the present bioresorbable polymers can include multilayered structures. Such structures may be in combinations with adhesive layers, hydrophobic or hydrophilic backing layers, or layers serving other purposes. In addition, the components of the various layers may form a composite material at the interface of the layer including the present bioresorbable polymer and the adhesive layer.

FIG. 1 depicts a composite bioresorbable patch utilizing the polymers of the invention.

The polymers of the present invention may be formed into films or other structures and layered or combined with other polymers. For instance, a film made from the present polymers can be combined with a second component, where the second component may be, for example, an adhesive polymer. The polymer/adhesive composition may take a layered structure, and/or may be combined with the other polymer to form a composite structure. When layers of the present polymer and another polymer are placed together, they may form a "hybrid composite layer" which denotes how the two layers interact at the interface, such as by forming a hybrid layer which includes a composite of the present polymer and the second component. Alternatively, the combination of the polymer of the present invention and, for example, an adhesive polymer could be as a homogeneous mixture. The second component should include one or many compounds containing isocyanate reactive functional groups. Isocyanate reactive functional groups may include, but are not limited to amines, hydroxyl groups, thiol groups, and carboxylic acids.

The adhesive polymer can include synthetic polymers and/or polysaccharides. The synthetic adhesive polymers may include polyvinyllactam, polyethylene glycol, polyethylene glycol-polypropylene glycol copolymers, vinyl acetate homo and copolymers, or poly(vinylalcohol). The polysaccharides may include starch, dextran, agar, cellulose, carboxymethyl cellulose (CMG), hydroxypropyl cellulose (HPC), chitin, chitosan, alginic acid, hyaluronic acid, chondroitin sulfate, heparin, their salts, or mixtures thereof.

The polymers when combined with other polymers may also use a compatibilizing agent. Such compatibilizing agents may include hydrogen bonding materials, such as water, low molecular weight compounds. Low molecular weight compounds which may be used as compatibilizing agents include diols, amines, thiols, carboxylic acids. Compatibilizing agents may also include PEO and/or PPO containing oligomers, polymers or copolymers.

Nitrogen containing polymeric compounds may also be included in the second component. Such nitrogen containing polymeric compounds may include quaternary ammonium containing copolymers of N-vinyl pyrrolidone that may or may not contain reactive groups such as aldehydes as described in EP 1 680 546 B1, which is incorporated by reference.

Likewise, one or more hemostatic agents may be included in t he second component. Specific hemostatic agents include oxidized cellulose, gelatin, collagen, and others.

Overall, the strength of the present polymers and/or compositions which include the present polymers can be adjusted to suit the intended use of the polymer. The term "strength" or "mechanical strength" describes favorable mechanical and/or physical characteristics of the present polymers and reflects the fact that preferred polymers for use in the present invention (generally, as films) having a mechanical strength which is sufficient to allow a suture to be used to anchor the polymer to a tissue site without appreciable tearing or ripping of the film.

Active ingredients or active agents can also be added to the present bioresorbable polymers. Exemplary bioactive agents which may be delivered pursuant to the present invention include, for example, anticoagulants, for example heparin and chondroitin sulphate, fibrinolytics such as tPA, plasmin, streptokinase, urokinase and elastase, steroidal and non-steroidal anti-inflammatory agents such as hydrocortisone, dexamethasone, prednisolone, methylprednisolone, promethazine, aspirin, ibuprofen, indomethacin, ketoralac, meclofenamate, tolmetin, calcium channel blockers such as diltiazem, nifedipine, verapamil, antioxidants such as ascorbic acid, carotenes and alpha-tocopherol, allopurinol, trimetazidine, antibiotics, especially noxythiolin and other antibiotics to prevent infection, prokinetic agents to promote bowel motility, that agents to prevent collagen crosslinking such as cis-hydroxyproline and D-penicillamine, and agents which prevent mast cell degranulation such as disodium chromolglycate, among numerous others.

In addition to the above agents, which generally exhibit favorable pharmacological activity related to promoting wound healing, reducing infection or otherwise reducing the likelihood that an adhesion will occur, other bioactive agents may be delivered by the polymers of the present invention include, for example, amino acids, peptides, proteins, including enzymes, carbohydrates, antibiotics (treat a specific microbial infection), anti-cancer agents, neurotransmitters, hormones, immunological agents including antibodies, nucleic acids including antisense agents, fertility drugs, psychoactive drugs and local anesthetics, among numerous additional agents. The delivery of these agents will depend upon the pharmacological activity of the agent, the site of activity within the body and the physicochemical characteristics of the agent to be delivered, and the therapeutic index of the agent, among other factors. One of ordinary skill in the art will be able to readily adjust the physicochemical characteristics of the present polymers and the hydrophobicity/hydrophilicity of the agent to be delivered in order to produce the intended therapeutic effect. The bioactive agents are administered in concentrations or amounts, which are effective to produce an intended result. The polymeric composition according to the present invention can be used to accommodate a broad range of hydrophilic and hydrophobic bioactive agents deliver them to sites in the patient.

Biomedical Applications of the Disclosed Compositions:

The invention is also directed to a bioresorbable patch comprising
(a) an adhesion barrier component comprising a composition according to the invention in the form of a film; and
(b) n adhesive component comprising:
   i) at least one synthetic adhesive polymer; and/or
   ii) at least one polysaccharide.

Preferably, the adhesive polymer is at least one synthetic polymer member selected from the group consisting of, polyvinyllactam, polyethyleneglycol, polyethylene glycol-polypropylene glycol copolymers, vinyl acetate homo and copolymers, and poly(vinyl alcohol) and blends thereof and the polysaccharide is at least one member selected from the group consisting of, starch, dextran, agar, cellulose, carboxymethyl cellulose (CMC), hydroxypropylcellulose (HPC), chitin, chitosan, alginic acid, hyaluronic acid, chondroitin sulfate, heparin, or their salts and blends thereof.

The bioresorbable patch can further comprise at least one compatibilizing component, which is at least one member selected from the group consisting of hydrogen-bonding materials. The hydrogen-bonding material is at least one member selected from the group consisting of water, diols, amines, thiols, carboxylic acids, poly(ethyleneoxide (PEO) and/or poly(propyleneoxide (PPO) containing oligomers, polymers and copolymers.

The bioresorbable patch can further comprise a hybrid composite layer at the interface between the adhesion barrier and the adhesive layers, wherein the said hybrid composite layer comprises of component (a) and component (b) of the bioresorbable patch. Preferably, component (b) comprises polyvinylpyrrolidone.

The bioresorbable patch can further comprise at least one bioactive agent.

Adhesion barrier application: A film of the compositions according to the invention can be employed for use as a barrier film to prevent post surgical tissue adhesion. The ratio of the hydrophilic polyethyleneoxide units to the hydrophobic degradable poly hydroxy carboxylic acid segments in the polymer and the extent of urethane/urea linkages can be controlled to obtain appropriate degradation profile and strength in the novel bioresorbable compositions. Solid polymeric compositions of Formula 1(a)-2(c) of this invention can be used as a bioresorbable adhesion barrier film to prevent post surgical adhesions.

The invention is further directed to a method of wound healing, comprising administering the composition according to the invention or the bioresorbable patch according to the invention to a patient in need thereof.

Preferably, said administration is a partial or total replacement for sutures or staples.

Wound Closure Application:

The composite bioresorbable patch of FIG. 1 can be used as a tissue adhesive patch with an adhesion barrier functionality to prevent adhesions in the extra vascular space following surgical procedures. The bioresorbable patch of this invention is constructed by integration of an adhesive on to an adhesion barrier. Solid polymeric compositions of Formula 1(a)-2(c) of this invention can be used as a bioresorbable adhesion barrier component and the adhesive component can be selected from the group containing at least one synthetic adhesive polymer and/or at least one polysaccharide compound. The bioresorbable patch can find particular use in sutureless closure of caesarean sections after infant delivery procedures. For surgical closure application, the disclosed bioresorbable adhesive patch construct of FIG. 1 is typically applied as a dry film to the moist tissue surface to support adhesive properties. Following utility of the adhesive component, the patch may be irrigated with saline solution or Ringer solution for supporting the adhesion barrier properties of the patch to prevent undesirable post-surgical adhesions.

Tissue engineering and wound healing application: The compositions disclosed in this invention can be made into porous bioresorbable scaffolds using methods known to those skilled in the art. A specific example of the porous scaffold that is desired is an open cell interconnected reticulated structure. The said construct can find utility as a medium to support rapid wound healing via application of vacuum. The porous constructs from the disclosed compositions along with supporting media can also be used in a vascular prosthesis device. Supporting media may include biological matrix proteins, or other components to promote endothelialization and tissue regeneration. Vascular prosthesis devices may include vascular access graft, a vascular shunt such as an arteriovenous shunt, a replacement for blood vessel, a bypass vascular prosthesis and other devices known to those skilled in the art.

The invention is further related to the use of the composition according to the invention as a component in a bioresorbable patch and/or for the treatment of diseases or conditions related to wound healing, wound closure, or tissue engineering.

Preferably, the composition according to the invention is used for the treatment of conditions related to post-surgical adhesions, for sutureless surgical closure, for the manufacture of an implantable medical device, for the manufacture of a bioresorbable patch, or for the treatment of diseases or conditions related to wound healing, wound closure, or tissue engineering.

Testing Procedures used in the following examples of the invention are described below:

Moisture Content:

The moisture content of the starting diol reactant was determined using the Karl-Fischer titration method per ASTM E203: Standard Test Method for Water Using Volumetric Karl Fischer Titration Hydroxyl Number and Molecular Weight of Diols:

The hydroxyl number of the dials were determined using ASTM D4274: Standard Test Methods for Testing Polyurethane Raw Materials: Determination of Hydroxyl Numbers of Polyols Isocyanate Content In the polymer and prepolymers was determined by titration using ASTM D2572: Standard Test Methods for Isocyanate Groups in Urethane Materials or Prepolymers Molecular Weights of Polymer:

Gel Permeation Chromatography (GPC) for all polymer samples were determined using guidelines set in ASTM D5296: Standard Test Method for Molecular Weight Averages and Molecular Weight Distribution of Polystyrene by High Performance Size-Exclusion Chromatography. GPC weight average molecular weight (Mw) and GPC number average molecular weight (Mn) in Daltons (Da) and the polydispersity index (PI=Mw/Mn) of the polyesters (A-B-A' polymer) were determined by Gel Permeation Chromatography (GPC) using polystyrene standards and tetrahydrofuran (THF) as the solvent at 30° C. GPC weight average molecular weight (Mw) and GPC number average molecular weight (Mn) in Daltons (Da) and the polydispersity index (PI=Mw/Mn) of the polyesterurethanes were determined by GPC using polystyrene standards and N,N-dimethylformamide (DMF) as the solvent at 40° C.

Tensile Strength:

Uniaxial tensile strength of polymeric bioresorbable film samples were tested for tensile load at break and elongation at break values on an Instron 5566 instrument at ambient temperature and relative humidity conditions using ASTM D1708: Standard Test Method for Tensile Properties of Plastics by Use of Microtensile Specimens.

Synthesis of Materials

Example 1

A-B-A' Polymer with Ratio of Ethylene oxide(EO):Lactide (LLA) of 4.0

Ymer N120 (Structure shown in Formula 4) (pendant MPEG based diol, MW=1090) is dried under $N_2$ sparging overnight at 105° C. The water content as measured using Karl-Fischer technique is <100 ppm. 10.32 g of the dried Ymer N120 is loaded into a three neck RBF in a $N_2$ glove box along with 8.44 g of L-lactide (Purac). The reaction vessel is setup with a $N_2$ inlet/outlet, a thermocouple thermometer equipped with a data logger and a glass shaft with Teflon stirrer coupled to a mechanical stirrer. The reaction vessel is immersed in an oil bath that is heated stepwise and gradually from room temp to 60° C. and then to 125° C. At 60° C., about 10 g of anhydrous diethyleneglycol dimethyl ether is added to the reaction mixture to bring it into a clear-colorless solution. Stannous octoate 0.051 g is added to the reaction mixture and the reaction temperature is ramped up to 125-130° C. The reaction mixture is held at this temperature for 3 hours at end of which the heating is stopped and the reaction mixture cooled to 70-75° C.

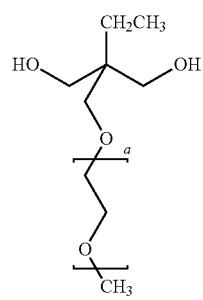

Formula 4

Ymer N120 (wherein a = 23-26)

Polyesterurethane (PEsU)—Chain Extended A-B-A' Polymer with Ratio of Ethylene Oxide(EO):Lactide (LLA) of 4.0

About 70 g anhydrous 1,4-dioxane is added to the above reaction mix at 70-75° C. with continuous stirring. To the resultant clear solution, 1.43 g of 1,6-hexamethylene diisocyanate (HDI) is added and the reaction is allowed to continue for ~6 hours until the —NCO value reached the theoretical expected number (as measured by ASTM D2572-97 Standard Test Methods for Isocyanate Groups in Urethane Materials or Prepolymers). At the end of the reaction a viscous mass resulted and the heat is cut off allowing the reaction mixture to cool to room temperature. Additional anhydrous 1,4 dioxane is added to reduce the viscosity and the polymer crashed into isopropyl alcohol. In this case, a viscous polymer solution separated out and settled to the bottom of the extraction vessel. The supernatant liquid is decanted and the polymer solution is dried first at room temperature under vacuum for 24-36 h and then the temperature is slowly raised to 40° C. and the drying continued for additional 72 h under vacuum. At the end of the drying operation, the oven is cooled to room temperature and the vacuum broken with $N_2$. The resultant polymer is a viscous liquid of MW of 54,253 daltons (Mn) that flows very slowly at room temperature, and has the formula shown in Formula 5.

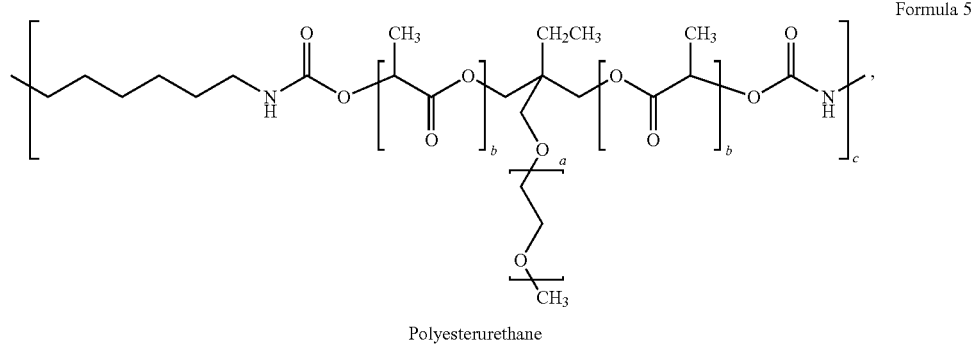

Formula 5

Polyesterurethane

Example 2

A-B-A' Polymer with Ratio of Ethylene Oxide(EO):Lactide (LLA) of 2.0

Ymer N120 [Structure shown in Formula 4] (pendant MPEG based diol, MW=1090) is dried under $N_2$ sparging overnight at 105° C. The water content as measured using Karl-Fischer technique is <100 ppm. 7.45 g of the dried Ymer N120 is loaded into a three neck RBF in a $N_2$ glove box along with 12.19 g of L-lactide (Purac). The reaction vessel is setup with a $N_2$ inlet/outlet, a thermocouple thermometer equipped with a data logger and a glass shaft with Teflon stirrer coupled to a mechanical stirrer. The reaction vessel is immersed in an oil bath that is heated stepwise and gradually from room temp to 60° C. and then to 125° C. At 60° C., about 10 g of anhydrous diethyleneglycol dimethyl ether is added to the reaction mixture to bring it into a clear-colorless solution. Stannous octoate 0.073 g is added to the reaction mixture and the reaction temperature is ramped up to 125-130° C. The reaction mixture is held at this temperature for 3 hours at end of which the heating is stopped and the reaction mixture cooled to 70-75° C.

Polyesterurethane (PEsU)—Chain Extended A-B-A' Polymer with Ratio of Ethylene Oxide(EO):Lactide (LLA) of 2.0

About 70 g anhydrous 1,4-dioxane is added to the above reaction mix at 70-75° C. with continuous stirring. To the resultant clear solution, 1.04 g of 1,6-hexamethylene diisocyanate (HDI) is added and the reaction is allowed to continue for ~6 hours until the —NCO value reached the theoretical expected number (as measured by ASTM D2572 Standard Test Methods for Isocyanate Groups in Urethane Materials or Prepolymers). At the end of the reaction a viscous mass resulted and the heat is cut off allowing the reaction mixture to cool to room temperature. Additional anhydrous 1,4 dioxane is added to reduce the viscosity and the polymer crashed into isopropyl alcohol yielding a white precipitate. The precipitate is filtered and under dried vacuum for 24 h and then the temperature is slowly raised to 40 C and the drying continued for additional 72 h under vacuum. At the end of the drying operation, the oven is cooled to room temperature and the vacuum broken with $N_2$. The resultant polymer is in the form of white flakes, of MW of 61,429 daltons (Mn) and has the following formula shown in Formula 5.

Example 3

A-B-A' Polymer with Ratio of Ethylene Oxide(EO):Lactide (LLA) of 0.5

Ymer N120 [Structure shown in Formula 4] (pendant MPEG based dial, MW=1090) is dried under $N_2$ sparging overnight at 105° C. The water content as measured using Karl-Fischer technique is <100 ppm. 2.60 g of the dried Ymer N120 is loaded into a three neck RBF in a $N_2$ glove box along with 16.99 g of L-lactide (Purac). The reaction vessel is setup with a $N_2$ inlet/outlet, a thermocouple thermometer equipped with a data logger and a glass shaft with Teflon stirrer coupled to a mechanical stirrer. The reaction vessel is immersed in an oil bath that is heated stepwise and gradually from room temp to 60° C. and then to 125° C. At 60° C., about 10 g of anhydrous diethyleneglycol dimethyl ether is added to the reaction mixture to bring it into a clear-colorless solution. Stannous octoate 0.102 g is added to the reaction mixture and the reaction temperature is ramped up to 125-130° C. The reaction mixture is held at this temperature for 3 hours at end of which the heating is stopped and the reaction mixture cooled to 70-75° C.

Polyesterurethane (PEsU)—Chain Extended A-B-A' Polymer with Ratio of Ethylene Oxide(EO):Lactide (LLA) of 0.5

About 70 g anhydrous 1,4-dioxane is added to the above reaction mix at 70-75° C. with continuous stirring. To the resultant clear solution, 0.41 g of 1,6-hexamethylene diisocyanate (HDI) is added and the reaction is allowed to continue for ~6 hours until the —NCO value reached the theoretical expected number (as measured by ASTM D2572 Standard Test Methods for Isocyanate Groups in Urethane Materials or Prepolymers). At the end of the reaction a viscous mass resulted and the heat is cut off allowing the reaction mixture to cool to room temperature. Additional anhydrous 1,4 dioxane is added to reduce the viscosity and the polymer crashed into isopropyl alcohol yielding a white precipitate. The precipitate is filtered and under dried vacuum for 24 h and then the temperature is slowly raised to 40 C and the drying continued for additional 72 h under vacuum. At the end of the drying operation, the oven is cooled to room temperature and the vacuum broken with $N_2$. The resultant polymer is in the form of white flakes, of MW of 203,445 daltons (Mn) and has the following formula shown in Formula 5.

Example 4

Film Formation and Testing Data 10 g of the synthesized polymer from Example 1,2 or 3 are dissolved in dichloromethane to yield 40 g of viscous solution (25 wt % solids). The solution is cast into a film on silicone coated Mylar using a Gardner blade coater to yield 10 mil films after drying in an inert atmosphere of $N_2$. Dog bones are cut from the dried film and used for tensile testing to determine the Tensile load at break and Elongation at break values according to ASTM D1708. The number average molecular weights of the polymers are determined using GPC according to ASTM D5296.

The physical properties of the A-B-A' polymers and Polyesterurethane (PEW polymers are summarized in Table 1.

TABLE 1

Physical properties of the A-B-A' polymers and Polyesterurethane polymers

| EO/ LLA Ratio | Polyester GPC Mn, Da (PI) | PEsU GPC Mn, Da (PI) | Tensile Load at break, N | Elongation at break, % |
|---|---|---|---|---|
| 0.5 (Ex. 4.1) | 11,875 (1.38) | 203,445 (1.90) | 18.06 | 208 |
| 2.0 (Ex. 4.2) | 5,554 (1.09) | 61,429 (1.66) | 0.03 | 42 |
| 4.0 (Ex. 4.3) | 3,411 (1.19) | 54,253 (1.71) | Highly Viscous Liquid | |

Solid polymers of this invention, such as Examples 4.1 and 4.2 in Table 1 above, are suitable candidates for use as a barrier film component for construction of a bioresorbable patch.

Example 5

Procedure for Construction of a Bioresorbable Adhesive Patch Device

A bioresorbable patch of the invention can be prepared by a method as shown in the following scheme 1:

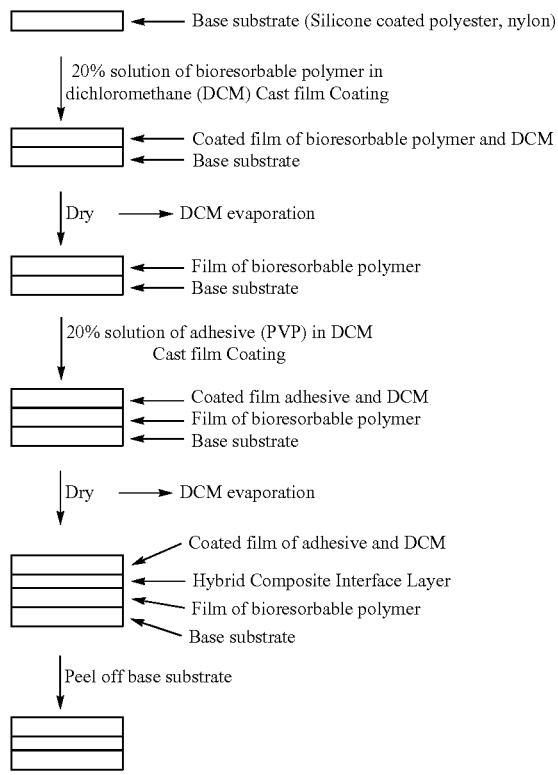

Composite bioresorbable adhesive patch

Scheme 1, Process for the Construction of Composite Bioresorbable Patch.

According to the method set forth in scheme 1, a base substance is coated with a bioresorbable polymer of the invention (such as a 20% solution) in combination with a solvent (such as DCM). The obtained coated substance is dried, and the dried product is coated with a solution of the desired adhesive (such as 20% solution of PVP), and then dried. The dried product is then separated/peeled off of the base substrate to provide the final product patch.

The adhesion barrier polymer (Component 1) was first dissolved in dichloromethane (DCM) to make a 20 wt % solution which was cast into a thin film (5-10 mil thickness), using a Gardner blade coater, on a base film substrate and dried completely under inert atmosphere. The base substrate chosen in the patch construction was commercially available silicone coated polyester (Mylar) film. The adhesive (Component 2) was also made into a 20 wt % solution in DCM and coated on the above dried barrier film followed by drying at room temperature. The resulting bioresorbable adhesive patch was easily peeled off from the base substrate for use in closure applications. The bioresorbable adhesive patch construct was robust and did not delaminate upon storage. Due to the solubility of both the adhesion barrier and the adhesive component in DCM, an integrated patch is formed as a result of a composite layer, linking the two functional components of the bioresorbable patch. The bioresorbable patch structure can be visualized as a three layered construct (see Scheme 1) wherein the adhesion barrier and the adhesive is integrated through the hybrid composite interfacial layer. Additionally the formation of the composite interfacial layer is enhanced due to the compatibilizing effect of polyethyleneoxide present in the barrier to the adhesive polyvinylpyrrolidone layer.

The invention being thus described generically and with reference to specific embodiments, it will be readily apparent to those skilled in the art that the same may be varied in many ways.

The invention claimed is:

1. A composition comprising at least one polymer having the structure A-B-A', wherein A and A' may be the same or different and each is a degradable aliphatic polyester component and wherein B is the reaction product resulting from the reaction between (i) A and A' and (ii) a diol, having one or more pendant oligomeric or polymeric groups, wherein B includes a pendant oligomeric or polymeric oxyalkylene moiety.

2. The composition of claim 1 wherein A and A' each comprise a poly(hydroxy carboxylic acid).

3. The composition of claim 2, wherein said poly (hydroxy carboxylic acid) is a member selected from the group consisting of glycolide, lactide, β-propiolactone, β-butyrolactone, γ-butyrolactone, δ-valerolactone, ε-caprolactone, 1,5-dioxepan-2-one, pivalolactone and 1,4-dioxane-2-one.

4. The composition of claim 1, wherein the degradable polyester aliphatic comprises aliphatic polycarbonate segments within the A and A' chains in the A-B-A' structure.

5. The composition according to claim 1, wherein the at least one polymer having the structure A-B-' is chain extended with a diisocyanate compound to form a polyesterurethane.

6. The composition according to claim 1, wherein the at least one polymer having the structure A-B-A' is end-capped with a monofunctional isocyanate compound.

7. The composition of claim 1, wherein the at least one polymer having the structure A-B-A' is reacted with an excess of diisocyanate to form a reactive polyesterurethane prepolymer.

8. The composition of claim 7, wherein the reactive polyesterurethane prepolymer is reacted with water or a multifunctional chain extender group selected from the group consisting of an amino, hydroxyl, and thiol compound to generate a polyesterurethaneurea, polyesterurethane, or polyesterurethanethiourethane polymer.

9. The composition of claim 1, further comprising a bioactive agent.

10. The composition of claim 1, wherein the composition is in the form of a film.

11. The composition of claim 1, wherein the composition is in the form of a porous construct.

12. A composition comprising:
at least one polymer having the structure A-B-A', wherein A and A' may be the same or different and each is a degradable polyester component and wherein B is the reaction product resulting from the reaction between (i) A and A' and (ii) a diol, having one or more pendant oligomeric or polymeric groups, said at least one polymer being selected from the group consisting of the following:

Formula 1(a)

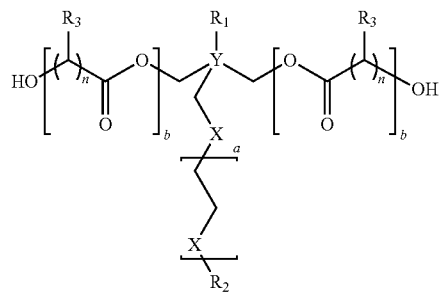

Formula 1(b)

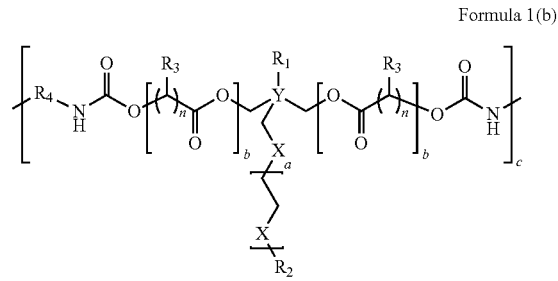

wherein X is O, S, or —CH2-,

Y is C or N,

R1 is H, an alkyl group containing 1-24 carbon atoms, a group containing an aromatic substituent or a group containing multiple alkylene oxide units of up to 500 units, R2 is alkyl group containing 1-12 carbon atoms, R3 is H, an alkyl group containing 1-24 carbon atoms, or an alkoxy group containing multiple alkylene oxide units of up to 500 units, R4 is a diisocyanate reaction fragment, n is 1-12, a is 2-500, b is 1-100, and c is 1-200;

Formula 1(c)

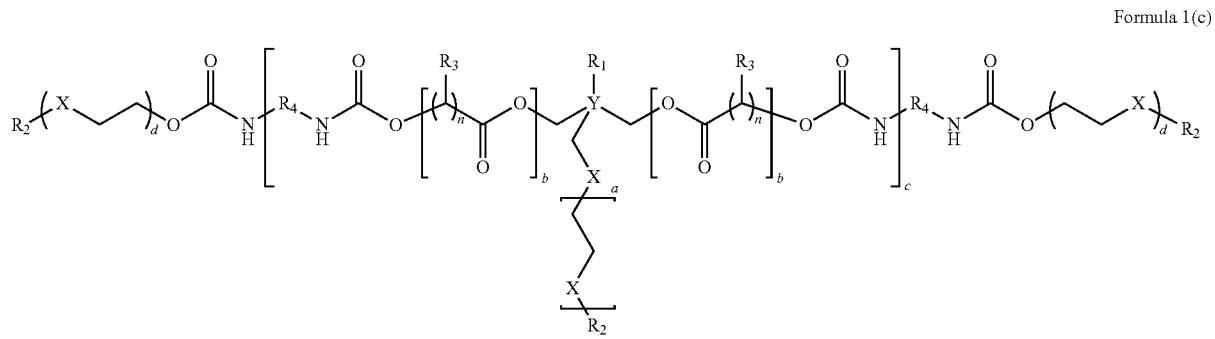

wherein X is O, S, or —CH2-,

Y is C or N,

R1 is H, an alkyl group containing 1-24 carbon atoms, a group containing an aromatic substituent or a group containing multiple alkylene oxide units of up to 500 units, R2 is alkyl group containing 1-12 carbon atoms, R3 is H, an alkyl group containing 1-24 carbon atoms, or an alkoxy group containing multiple alkylene oxide units of up to 500 units, n is 1-12, a is 2-500, and b is 1-100;

wherein X is O, S, or —CH2-,

Y is C or N,

R1 is H, an alkyl group containing 1-24 carbon atoms, a group containing an aromatic substituent or a group containing multiple alkylene oxide units of up to 500 units, R2 is alkyl group containing 1-12 carbon atoms or a silicone containing fragment, R3 is H, an alkyl group containing 1-24 carbon atoms, or an alkoxy group containing multiple alkylene oxide units of up to 500 units, R4 is a diisocyanate reaction fragment, n is 1-12, a is 2-500, b is 1-100, c is 1-200, and d is 4-300;

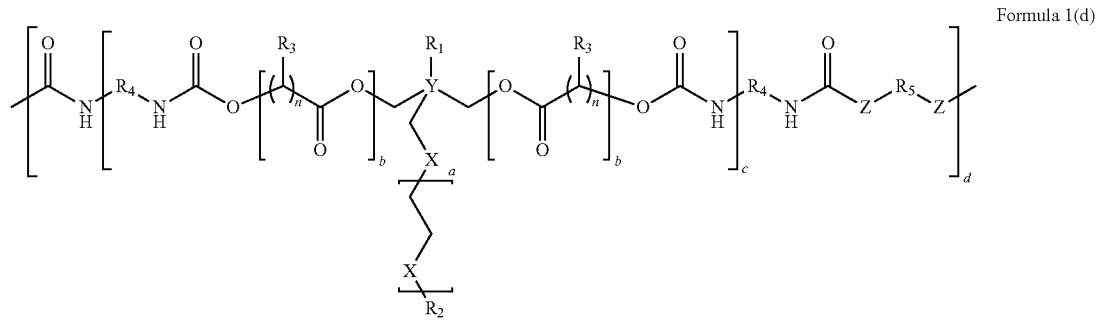

Formula 1(d)

wherein X is O, S, or —CH2-,
Y is C or N,
Z is O, S, NH, or an N-alkyl group,
R1 is H, an alkyl group containing 1-24 carbon atoms, a group containing an aromatic substituent or a group containing multiple alkylene oxide units of up to 500 units,
R2 is alkyl group containing 1-12 carbon atoms,
R3 is H, an alkyl group containing 1-24 carbon atoms, or an alkoxy group containing multiple alkylene oxide units of up to 500 units,
R4 is a diisocyanate reaction fragment,
R5 is an alkyl, silicone, alicyclic, heterocyclic, or an aromatic group,
n is 1-12,
a is 2-500,
b is 1-100,
c is 1-20, and
d is 4-300;

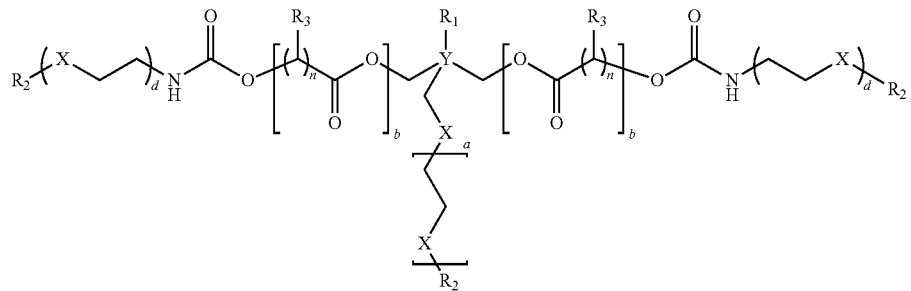

Formula 1(e)

wherein X is O, S, or —CH2-,
Y is C or N,
R1 is H or an alkyl group containing 1-24 carbon atoms, a group containing an aromatic substituent or a group containing multiple alkylene oxide units of up to 500 units,
R2 is alkyl group containing 1-12 carbon atoms or a silicone containing fragment,
R3 is H, an alkyl group containing 1-24 carbon atoms, or an alkoxy group containing multiple alkylene oxide units of up to 500 units,
a is 2-500,
b is 1-100, and
d is 4-300.

13. The composition according to claim 12, wherein the alkylene oxide unit is a poly(ethylene oxide) unit.

* * * * *